United States Patent
Volgyesi

Patent Number: 6,116,239
Date of Patent: Sep. 12, 2000

[54] INHALATION DEVICE

[75] Inventor: George Volgyesi, 36 Gatehead Rd., North York, Canada

[73] Assignees: Art Slutsky, Toronto; Noe Zamel, North York; George Volgyesi, Willowdale, all of Canada

[21] Appl. No.: 09/128,405

[22] Filed: Aug. 3, 1998

[30] Foreign Application Priority Data

Aug. 7, 1997 [CA] Canada .................................. 2212430

[51] Int. Cl.⁷ .................................................. A61M 15/00
[52] U.S. Cl. ............................... 128/203.15; 128/203.21
[58] Field of Search ..................... 128/203.12, 203.15, 128/203.21, 203.23

[56] References Cited

U.S. PATENT DOCUMENTS

| | | |
|---|---|---|
| 2,587,215 | 2/1952 | Priestly . |
| 2,603,216 | 7/1952 | Taplin et al. . |
| 2,672,865 | 3/1954 | Willis . |
| 3,362,405 | 1/1968 | Hazel ................................ 128/203.15 |
| 3,938,516 | 2/1976 | Mathes . |
| 3,964,483 | 6/1976 | Mathes . |
| 3,973,566 | 8/1976 | Mathes . |
| 3,980,074 | 9/1976 | Watt et al. . |
| 4,005,711 | 2/1977 | Glenn . |
| 4,014,336 | 3/1977 | Mathes . |
| 4,098,273 | 7/1978 | Glenn . |
| 4,216,768 | 8/1980 | Jack . |
| 4,227,522 | 10/1980 | Carris . |
| 4,307,734 | 12/1981 | Blankenship . |
| 4,524,769 | 6/1985 | Wetterlin . |
| 5,042,472 | 8/1991 | Bunin . |
| 5,309,900 | 5/1994 | Knoch et al. .................... 128/200.14 |
| 5,331,953 | 7/1994 | Andersson et al. ............... 128/203.15 |
| 5,458,135 | 10/1995 | Patton et al. ..................... 128/200.14 |
| 5,476,093 | 12/1995 | Lankinen . |
| 5,590,645 | 1/1997 | Davies et al. . |
| 5,596,982 | 1/1997 | Blaha-Schnabel ................ 128/200.14 |
| 5,615,670 | 4/1997 | Rhodes ............................. 128/203.15 |
| 5,653,227 | 8/1997 | Barnes et al. . |
| 5,657,749 | 8/1997 | Cox . |
| 5,660,169 | 8/1997 | Kallstrand et al. ............... 128/203.15 |
| 5,692,496 | 12/1997 | Casper et al. . |
| 5,740,793 | 4/1998 | Hodson et al. . |
| 5,765,552 | 6/1998 | Zanen et al. ...................... 128/203.15 |
| 5,785,049 | 7/1998 | Smith et al. ...................... 128/203.21 |
| 5,829,434 | 11/1998 | Ambrosio et al. ................ 128/203.15 |
| 5,896,855 | 4/1999 | Hobbs et al. ..................... 128/203.21 |
| 5,947,117 | 9/1999 | Herold et al. .................... 128/203.21 |

FOREIGN PATENT DOCUMENTS

| | | |
|---|---|---|
| 1118341 | 7/1968 | United Kingdom . |
| WO 93/00951 | 1/1993 | WIPO . |

*Primary Examiner*—John G. Weiss
*Attorney, Agent, or Firm*—Brinks Hofer Gilson & Lione

[57] ABSTRACT

An inhalation device for use in delivering a powdered substance to a user, the inhalation device comprises a housing including a holding portion for holding the substance; an air entry passageway sized and configured to direct air entering the inhalation device at the portion and to fluidize the substance upon inhalation by the user; a hold-up chamber in flow communication with the holding portion for receiving the fluidized substance and maintaining the substance in a fluidized state during inhalation by the user; and an air exit passageway in flow communication with the hold-up chamber and adapted to deliver the substance to the user.

44 Claims, 9 Drawing Sheets

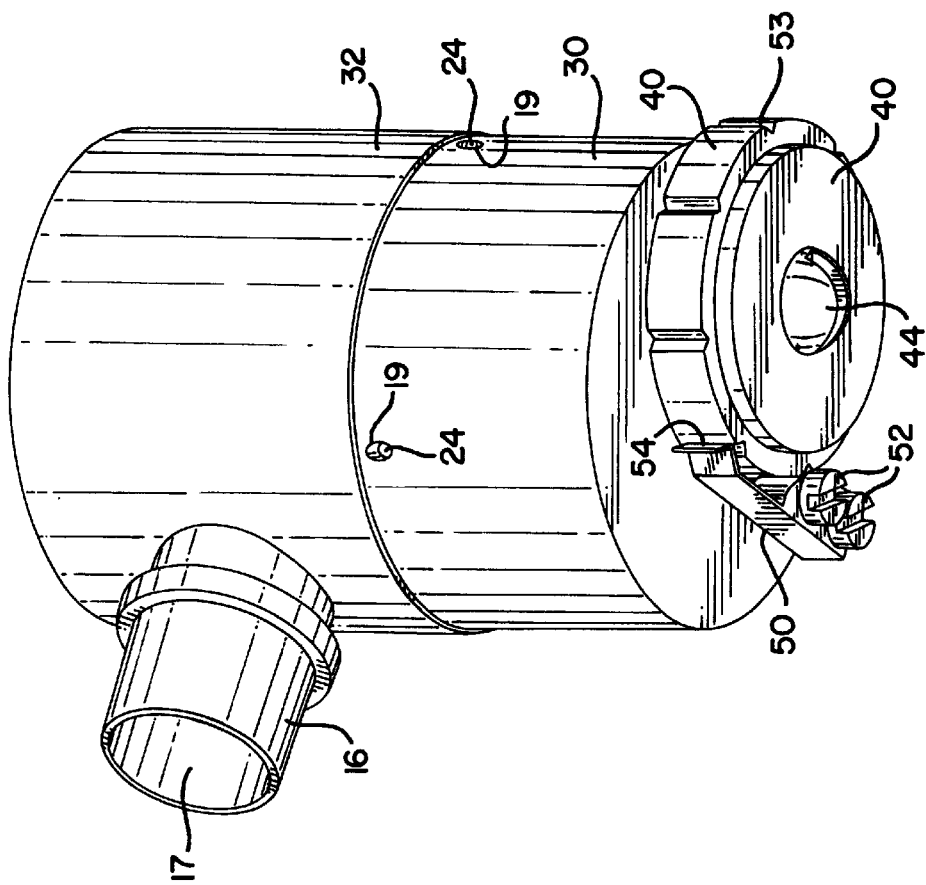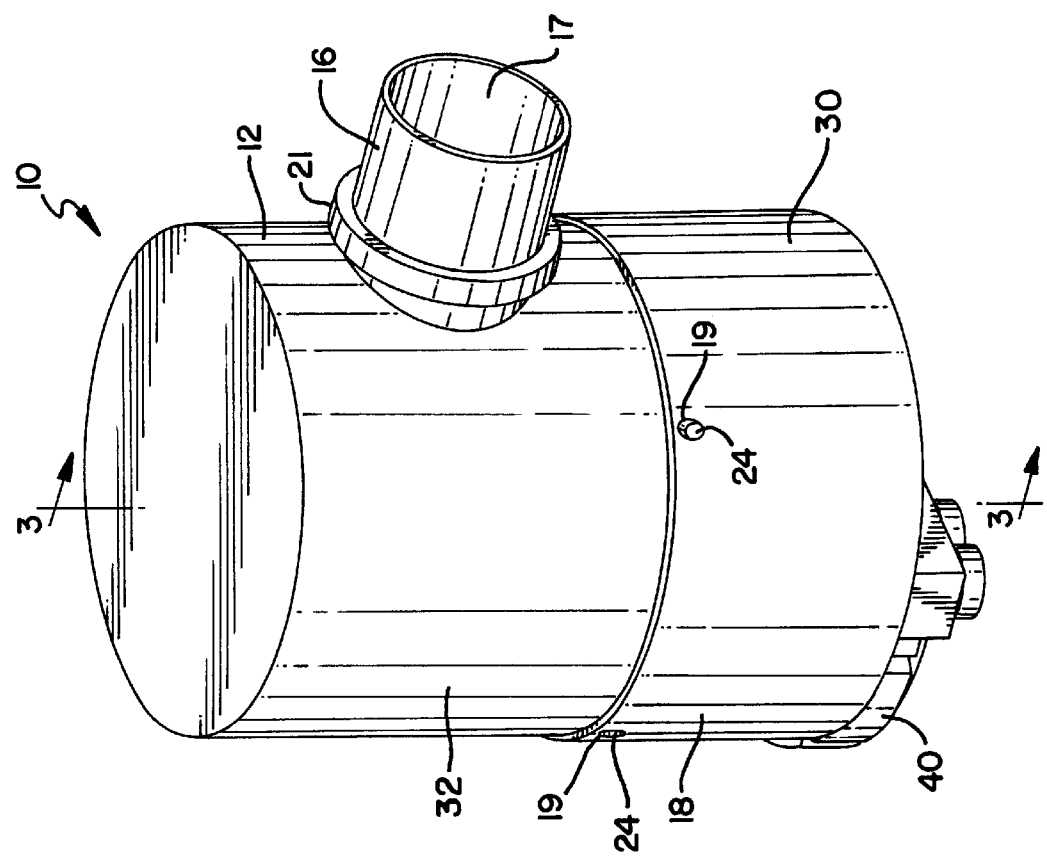

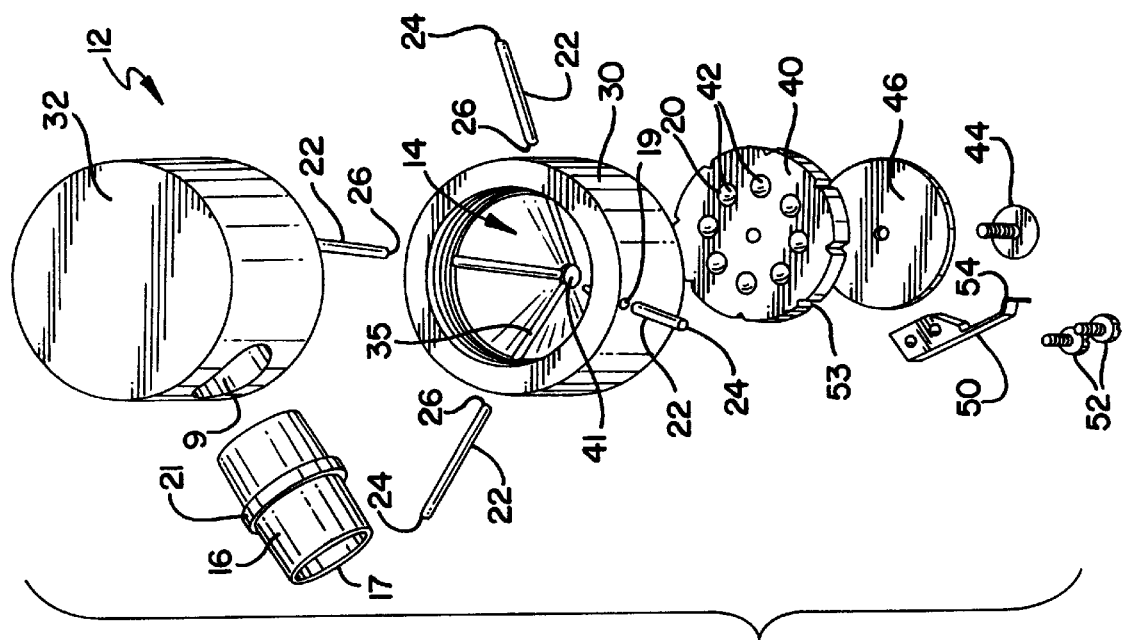
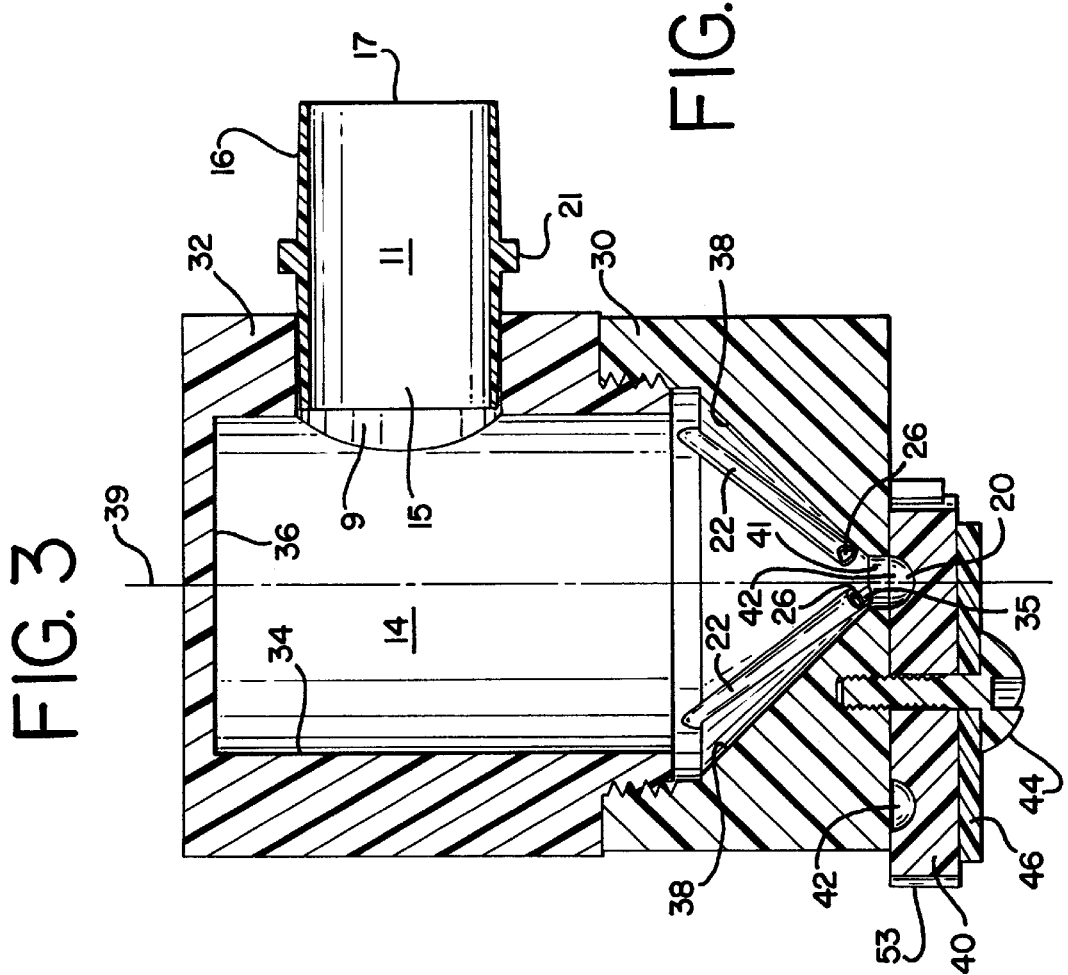

TOTAL FLOW = 8 L/min.
RESISTANCE = 0.3 cm H2O/L/min.

TOTAL FLOW = 8 L/min.
RESISTANCE = 0.3

INHALATION DEVICE

FIELD OF THE INVENTION

This invention relates to devices for the administration of a powdered substance by inhalation, and in particular, to a device for administering powdered medicaments to the lungs of a user.

BACKGROUND OF THE INVENTION

Various types of inhalers for delivering a medicament are known. For example, U.S. Pat. No. 3,938,516 (Mathes No. 1) discloses an inhaler for delivering a powdered medicament. The device includes a mouth piece 14 which has provided therein an emptying chamber. A longitudinally extending passageway for introducing air into the inhaler is connected to the passageway. The inhaler also includes a hollow air stream tube which extends preferably into an opened capsule containing a medicament. Upon inhalation, air drawn through the air stream tube into the capsule assists in causing the medicament to be expelled therefrom.

Mathes No. 1 states at column 4, lines 32–45, that "Quite obviously, no single device will be suitable for all persons requiring administration of powdered medicaments since, for example, people with differing lung capacities are known to generate flow rates from about 30 liters/minute or so to about 120 liters/minute or so through inhalation devices of this and known types. Nonetheless, the device of [Mathes No. 1] affords such variability, through proper selection of the various design parameters, that a device, embraced with the scope of [Mathes No. 1], can be designed for a particular patient-generated flow rate to deliver the medicament according to a certain set of pre-determined objectives (e.g., slow or fast administration, one or more inhalations etc.)."

Accordingly, one of the disadvantages of Mathes No. 1 is that a single device is not capable of being used with a variety of patients. In some cases, the inhaler may be required for treating an individual who has a diminished lung capacity. For example, an individual who may need to use the device may suffer from, for example, emphysema or asthma, and may not be able to generate a high flow rate of air. Therefore, the device of Mathes No. 1 would have to be designed for someone who could only administer a dose slowly due to their diminished lung capacity. Alternately, the device may be used by someone who does not have a diminished lung capacity. Unless the device is properly designed, the medicament will exit the inhaler at a rate such that a portion, if not substantially all of the medicament, will impact upon the throat and airways of the user and therefore not be drawn into the lungs for absorption.

A further disadvantage of Mathes No. 1 is that, over the course of a single inhalation, the concentration of the medicament in the air inhaled by a user is uneven. This arises for two reasons. First, once the medicament is withdrawn from the container, it is immediately transported through the inhaler into the mouth or nose of the user. Therefore, little mixing of the medicament in the air inhaled by the user occurs. This results in uneven distribution of the powder in the air inhaled by the user and, to the extent that the medicament is drawn into the lungs of the user, the medicament will not be distributed evenly throughout the lungs. Secondly, a substantial portion of the medicament may be withdrawn from the medicament container and entrained in the air upon initial inhalation. Accordingly, the medicament will not be distributed throughout the entire lung of the user but will be concentrated in that portion of the lungs of the user to which the first portion of the air inhaled on inhalation travels. (See also U.S. Pat. No. 4,014,336 (Mathes No. 2); U.S. Pat. No. 4,005,711 (Glen No. 1); and U.S. Pat. No. 4,098,273 (Glen No. 2).) In Glen Nos. 1 and 2, a deflector surface is used to direct a portion of the incoming air into the medicament container so as to entrain the medicament in the air which is inhaled by a user.

U.S. Pat. No. 3,964,483 (Mathes No. 3) and U.S. Pat. No. 3,973,566 (Mathes No. 4) each disclose a device wherein the air entering the inhaler is not aimed directly at the medicament in a medicament container. Instead, turbulent air flow is created so as to draw the medicament out from the container. These devices have the same disadvantages as Mathes No. 1.

SUMMARY OF THE INVENTION

In accordance with the instant invention, there is provided an inhalation device for use in delivering a powdered substance to a user. The inhalation device comprises a holding portion for holding the substance, an air entry passageway, a hold-up chamber and an air exit passageway. The air entry passageway is sized and configured to direct air entering the inhalation device at the holding portion and to fluidize the substance upon inhalation by the user.

In one embodiment, the air entry passageway includes an inlet port, an exit port and a cross-sectional flow area. The exit port is proximate to and directed at the holding portion. The hold-up chamber is in flow communication with the holding portion. The air exit passageway preferably includes an inlet port in flow communication with the hold-up chamber, an exit port and a cross-sectional flow area. The cross-sectional flow area of the exit passageway is preferably greater than the cross-sectional flow area of the air entry passageway.

In a preferred embodiment of the invention, the inhalation device includes a plurality of air entry passageways, with at least one of the air entry passageways directed at the holding portion. The number and cross sectional flow area of the air entry passageways may be selected to cause the air entering the inhalation device through the air entry passageways to travel at a velocity to fluidize a major portion of the powdered substance, preferably a medicament, upon the commencement of inhalation by the user. In a more preferred embodiment, substantially all of the powdered substance is fluidized upon commencement of the inhalation by the user. The combined cross-sectional flow area of the plurality of air entry passageways is preferably less than the cross-sectional flow area of the air exit passageway.

Accordingly, one advantage of the instant invention is that the air entering the inhaler effectively forms a jet directed to impinge upon the powdered substance in the inhaler so as to cause the substance to effectively immediately fluidize during the first stage of inhalation by the user. The fluidized substance is then drawn into the hold-up chamber where it is effectively stored in a fluidized state during the remainder of the inhalation. This produces three advantages.

First, the powdered substance is effectively deaggregated almost immediately upon inhalation so as to form a relatively uniform concentration of substance in the hold-up chamber at the commencement of inhalation. As air is drawn through the air exit passageway by the user, a relatively constant concentration of substance is initially drawn into the lungs of the user. The fluidized substance is thereafter diluted over time as more air is drawn into the hold-up chamber. Therefore, the concentration of the first portion of the fluidized substance initially inspired by the user will be greater than the subsequent portions, which helps to provide a more even deposition of the substance in the lungs of the user.

Secondly, the deaggregation of the particles by the air travelling through the air entry passageways reduces the likelihood of large particles of substance being present and impacting upon the throat and/or upper airways of the user.

A third advantage is that the relatively even concentration of substance in the hold-up chamber is formed almost immediately upon inhalation so that even the first air drawing into the lungs of the user contains a diluted fluidized mass of substance. Further, as the inhalation continues, additional air is introduced through the air entry passageways into the hold-up chamber to mix with the remaining fluidized substance. Therefore, as the inhalation continues, the substance is continuously drawn into the lungs. Thus, the substance is drawn into a large volume of the lung.

In one embodiment, substantially all of the air entering the inhalation device is directed at the powdered substance. In a further alternate embodiment, all of the air entering the inhalation device is directed at the substance.

The air exit passageway is preferably sized, with a cross-sectional flow area greater than the cross-sectional flow area of the combined air entry passageways, to provide the fluidized substance leaving the inhalation device with a velocity sufficiently low for a major proportion of the substance not to impact on the throat and upper airways of the user but to be drawn into the lungs and/or lower passageway of the user. The air which enters the inhalation device at a rapid velocity through the air entry passageways may decrease in velocity as it enters the hold-up chamber. The air may then be drawn off from the hold-up chamber at a controlled rate so as to provide a velocity of the fluidized substance leaving the hold-up chamber (through the air exit passageway) which is sufficiently low for the substance to be drawn into the lungs of the user.

The air entry passageway and/or the lower portion of the hold-up chamber are configured to introduce air into the hold-up chamber such that the air entering the inhalation device will rotate, swirl or travel around the hold-up chamber to maintain the substance in a fluidized state. In one embodiment, the hold-up chamber has interior walls which are substantially smooth and are of generally uniform cross-section. Accordingly, the hold-up chamber is preferably configured to permit cyclonic flow of air within the hold-up chamber and the air entry passageway and/or the lower portion of the hold-up chamber are configured to initiate cyclonic flow of air upon inhalation by the user. The cyclonic flow of air may assist in further deaggregation of the powdered substance and in maintaining the deaggregated substance in a fluidized state.

The air exit passageway is preferably positioned in the hold-up chamber at a position which is distal to the holding portion which receives the powdered substance. In one embodiment, the hold-up chamber is cylindrically shaped and has a longitudinally extending axis around which the air inhaled by a user rotates or swirls with the air exit passageway positioned on the cylindrically shaped wall of, and in flow communication with, the hold-up chamber. In this embodiment, the hold-up chamber extends longitudinally away from the holding portion which receives the powdered substance to the air exit passageway. The air exit passageway preferably extends outwardly from the hold-up chamber at an angle to the longitudinal direction of the hold-up chamber. More preferably, this angle is about 90° (i.e. transverse to the axis of rotation of the air in the hold-up chamber).

In another embodiment, the hold-up chamber further includes a frusto-conically shaped portion extending from the cylindrical portion. A bottom of the frusto-conically shaped portion communicates with the holding portion. The shape of the frusto-conically shaped portion facilitates the cyclonic flow of fluidized substance within the hold-up chamber.

In addition, in those embodiments including a plurality of air entry passageways, one or more of the plurality may be configured to direct air at the powdered substance and one or more of the air entry passageways may be configured to direct air so as to promote the cyclonic rotation of air in the hold-up chamber.

A further advantage of the instant invention is that high velocity air may be used to extract the powdered substance from a reservoir to mix the medicament with air and to segregate or deaggregate the substance. Further, this extraction, mixing and deaggregation may be achieved by inspiratory effort alone. No battery operated impellers or other mechanical devices need be included. Further, by utilizing a plurality of air entry passageways which, in total, have a relatively low cross-sectional area, these high velocities can be achieved using low inspiratory flow rates.

A further advantage is that the dosage which is withdrawn is less dependent on inspiratory flow rates than other known devices. Accordingly, the dose of powdered substance, preferably a medicament, which is withdrawn from the inhalation device is more consistent than may be achieved with other known devices. Further, due to the low velocity of substance as it exits the inhalation device, relatively low amounts of substance will be deposited in the throat and upper airways of the user. Not only does this result in more substance being drawn into the lungs of the user, where in general it is more easily absorbed by the body, it may cause less irritation to the throat and upper airways of the user.

BRIEF DESCRIPTION OF THE DRAWINGS

These and other advantages of the instant invention will be more fully and completely understood in conjunction with the following drawings of the presently preferred embodiments of the invention. Many of the features and dimensions portrayed in the drawings have been exaggerated for the sake of illustration and clarity.

FIG. 1 is a top perspective view of an inhalation device according to the instant invention.

FIG. 2 is a bottom perspective view of an inhalation device according to the instant invention.

FIG. 3 is a cross section along the line 3—3 in FIG. 1.

FIG. 4 is an exploded view of the inhalation device of FIG. 1.

FIG. 5 is a bottom view of the inhalation device of FIG. 1.

FIG. 6 is a perspective view of an alternative embodiment of the inhalation device according to the instant invention.

FIG. 7 is a cross section along the line 7—7 in FIG. 6.

FIG. 8 is a cross section along the line 8—8 in FIG. 6.

FIG. 9 is a cross-sectional view in the direction of line 3—3 of FIG. 1 of an alternate embodiment of the inhalation device according to the instant invention.

FIG. 10 is a cross-sectional view along line 10—10 in FIG. 9.

FIG. 11 is a cross-sectional view along line 11—11 in FIG. 9 showing the air entry passageways and the medicament cassette.

FIG. 12 is a cross-sectional view along the line 3—3 in FIG. 1 of a second alternate embodiment of the inhalation device.

FIG. 13 is a cross-sectional view along the line 3—3 in FIG. 1 of a third alternate embodiment of the inhalation device.

DETAILED DESCRIPTION OF THE PRESENTLY PREFERRED EMBODIMENTS

Figure 5:
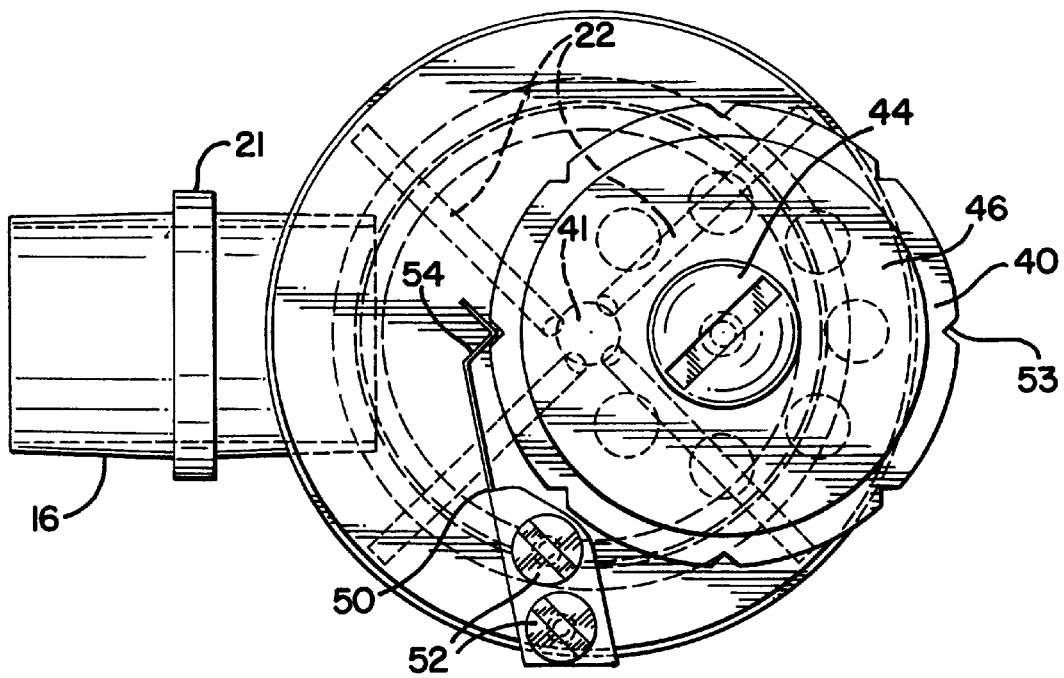
Figure 6:
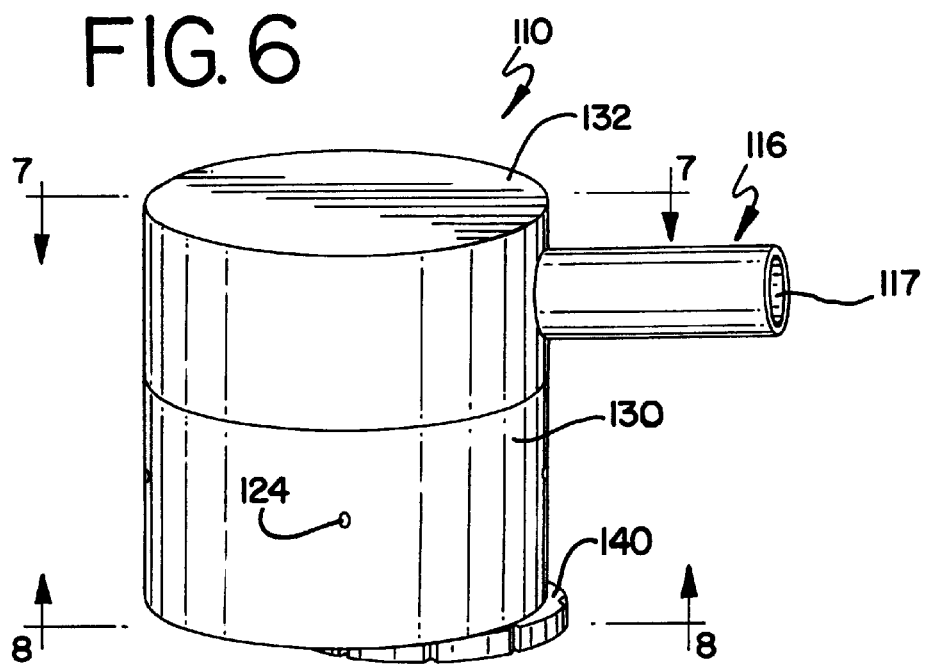

As shown in FIGS. 1–4, inhaler 10 comprises a housing 12 having a hold-up chamber 14, a mouthpiece 16 and a holding portion 20 to receive and hold a substance, and more specifically, a powdered substance. The powdered substance is preferably a medicament, which is generally defined as a substance used in therapy, and more specifically as a substance used to treat various ailments, diseases, etc. and/or to relieve pain, although it should be understood that the present invention would also work with other powdered substances. Examples of dry powdered medicaments that can be used with the present invention include, but are not limited to, antibiotics such as Erythromycin (for respiratory infections), Beta-Agonist (such as Ventolin (SALBUTAMOL)), Corticosteroid (such as Flovent (FLUTICASONE)), Cromoglycate (such as Intal (Sodium Cromoglycate)), and antihistamines (such as Dimetene (Brompheniramine Maleate)).

Housing 12 may be of any particular shape or exterior configuration. Accordingly, provided the hold-up chamber is of an appropriate dimension and internal configuration, the inhaler may be shaped to suit various aesthetic requirements. Further, housing 12 may be made from any material which is known in the art. Preferably, housing 12 is made from a material, such as a thermal plastic, which will prevent the build up of static electricity so as to minimize adherence of the substance to the internal walls of housing 12. Alternately, or in addition, the interior walls of housing 12 may be coated with a material, known to those of skill in the art, to reduce the adherence of the substance to the internal walls of housing 12. It should be understood by those skilled in the art that other materials would also work, and that the above-material is meant to be illustrative, rather than limiting.

Holding portion 20 is preferably sized so as to receive therein a single dose of powdered substance, or medicament. Holding portion 20 may be provided at any particular location in housing 12. However, it is preferably positioned such that, when inhaler 10 is to be used, holding portion 20 will be positioned at the bottom of housing 12 and will open facing upwardly into hold-up chamber 14 as shown in FIG. 3. This will assist in maintaining the substance in holding portion 20 while inhaler 10 is in use.

Housing 12 includes at least one air entry passageway 22 which is sized and configured to direct air entering inhaler 10 at holding portion 20 so as to at least substantially fluidize the substance upon inhalation by the user. Housing 12 may have a plurality of such air entry passageways. For example, housing 12 may have 1 to 8 air entry passageways and, more preferably, from 3 to 5 air entry passageways. As shown in FIGS. 3 and 4, housing 12 includes four such passageways 22. Each passageway 22 has an entry port 24 and an exit port 26. Air entry port 24 may be positioned at any point in or about housing 12. Preferably, each entry port 24 is located adjacent exterior surface 18 of housing 12, which includes port 19 that communicates with the entry port of the air entry passageway 22. Each exit port 26 may be positioned and/or each passageway 22 may be configured so as to direct air travelling through passageways 22 at the substance in holding portion 20 to fluidize or assist in fluidizing the substance positioned therein. Preferably, the exit port 26 is positioned immediately adjacent and proximate to the holding portion, or adjacent the edge of the holding portion, so as to direct air to impinge upon the substance in the holding portion.

In the exemplary embodiment shown in FIGS. 3 and 4, each air entry passageway 22 has a relatively uniform diameter and cross-sectional flow area throughout its length. The air entry passageways are preferably straight. In one suitable embodiment, the internal diameter of the air entry passageways is about 1.75 mm, which results in a cross-sectional flow area of approximately 2.405 $mm^2$ for each air entry passageway, and a total combined cross-sectional flow area of approximately 9.62 $mm^2$ for four air entry passageways. One of skill in the art should understand that other diameters, cross-sectional flow areas and/or cross-sectional shapes, such as a square, would also work.

Figure 20:
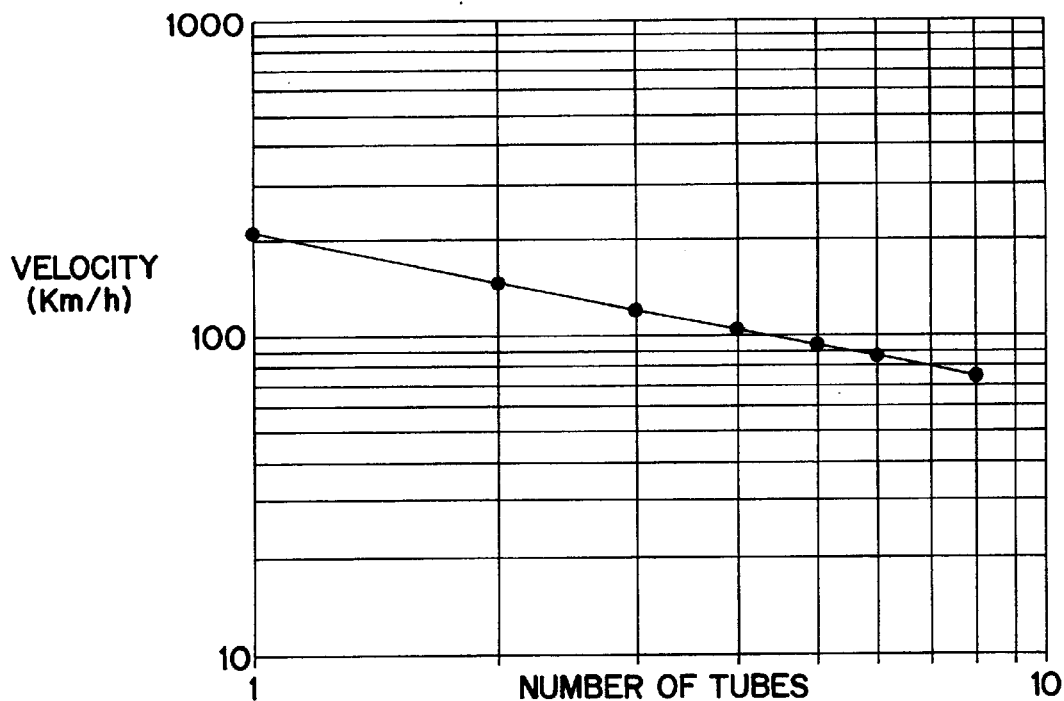
FIG. 20 is a graph of velocity (km/hr) and number of tubes for an inhalation device having a total resistance to flow of 0.3 cm $H_2O$/l/min and at a constant flow rate of 8 l/min.
Figure 21:
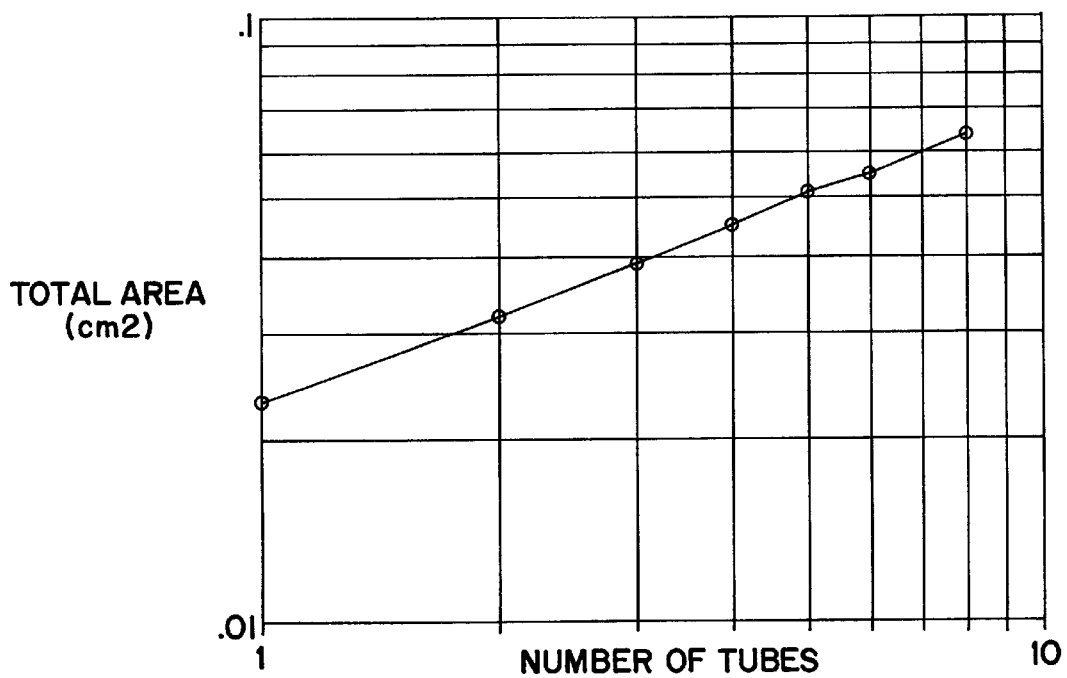
FIG. 21 is a graph of cross-sectional area of the air entry tubes ($cm^2$) versus the number of tubes for the device of FIG. 19.

Referring to FIG. 21, various tube configurations are shown as having total combined cross-sectional flow areas ranging from about 0.024 $cm^2$ (2.4 $mm^2$) for a single air entry passageway (tube) to about 0.064 $cm^2$ (6.4 $mm^2$) for eight air entry passageways (tubes). As is also well understood by those of skill in the art, the average velocity (km/hr) of the flow is equal to the volume flow rate (vol./hr) divided by the cross-sectional flow area. Accordingly, for example, a volume flow rate of 8 L/min through the various tube configurations (having cross-sectional flow areas of from about 0.024 $cm^2$ to about 0.064 $cm^2$) results in a flow rate (velocity) ranging from about 75 km/hr to about 210 km/hr as shown in FIG. 20. Although the minimum velocity required to fluidize the substance 20 is formulation dependent, generally a minimum flow rate of about 45 km/hr is sufficient to fluidize the types of medicament generally administered in dry powder form, with a more preferred minimum of about 60 km/hr.

Because the air entry passageways 22 are positioned immediately adjacent and proximate to and directed at the substance, the air flowing from the exit ports 24 impinges on the substance and extracts it from the holding portion 20 so as to thereby mix it in the air so as to produce a dust cloud in the chamber. The fluidization of the substance includes two distinct phases. First, the substance is deaggregated into separate respirable particles by the impinging air flow. Deaggregation is the separation of the substance particles, which may have a tendency to clump together. Preferably, most, if not all, of the particles are deaggregated to a size of less than 5.8 microns. Second, the substance particles are thereafter suspended in a stream of air or gas in the hold-up chamber. Fluidization is distinguished from a simple entrainment of the substance, wherein relatively large lumps of aggregated substance can be carried into and suspended in the air flow, either by suction from above or by air flowing through the substance. As the substance is fluidized, or impinged upon by the air scooping the substance out of the holding portion, the initial concentration of the substance in the cloud formed in the hold-up chamber is dependent on the nominal dose of the substance and the volume of the hold-up chamber.

As shown in FIGS. 3 and 4, the hold-up chamber 14 is in flow communication with and positioned immediately above holding portion 20. Hold-up chamber 14 is configured to maintain the substance in a fluidized state during inhalation by the user and may also be configured to assist in fluidizing the substance in holding portion 20. Hold-up chamber 14 is accordingly designed to produce or assist in producing an air flow pattern such that the substance may be readily deaggregated upon inhalation by the user and maintained in a deaggregated condition during inhalation. Preferably, hold-up chamber 14 is configured to produce a swirling or cyclonic air flow in hold-up chamber 14. Accordingly, in the preferred embodiment shown in FIG. 3, the housing 12 is provided with lower portion 30 and upper portion 32 that define the hold-up chamber 14. As shown in FIG. 3, the upper portion 32 is threadably secured to the lower portion 30. It should be understood, however, that the portions could be connected in any number of ways including, but not limited to a press-fit, a detent, an adhesive or any type of mechanical attachment. Alternatively, the upper and lower portions could be integrally formed as a single unit.

Lower portion 30 is provided with angled walls 38. In an exemplary embodiment, the walls are angled at about an angle of approximately 45 degrees, although it should be understood that other configurations and angles would also work. By angling walls 38, a lower portion of hold-up chamber 14 has a frusto conical shape so as to encourage the cyclonic or swirling flow of air in hold-up chamber 14. Further, the configuration and orientation of passageways 22 may be such as to encourage the formation of the cyclonic air flow. As shown in FIG. 3, passageways 22 are preferably spaced around lower portion 30 and are straight. It will be appreciated that provided a cyclonic or swirling flow of air is produced, any particular configuration may be provided to passageways 22 and the internal surfaces of lower portion 30. For example, passageways may be curved to direct at least a portion of the air tangentially into the hold-up chamber.

Figure 7:
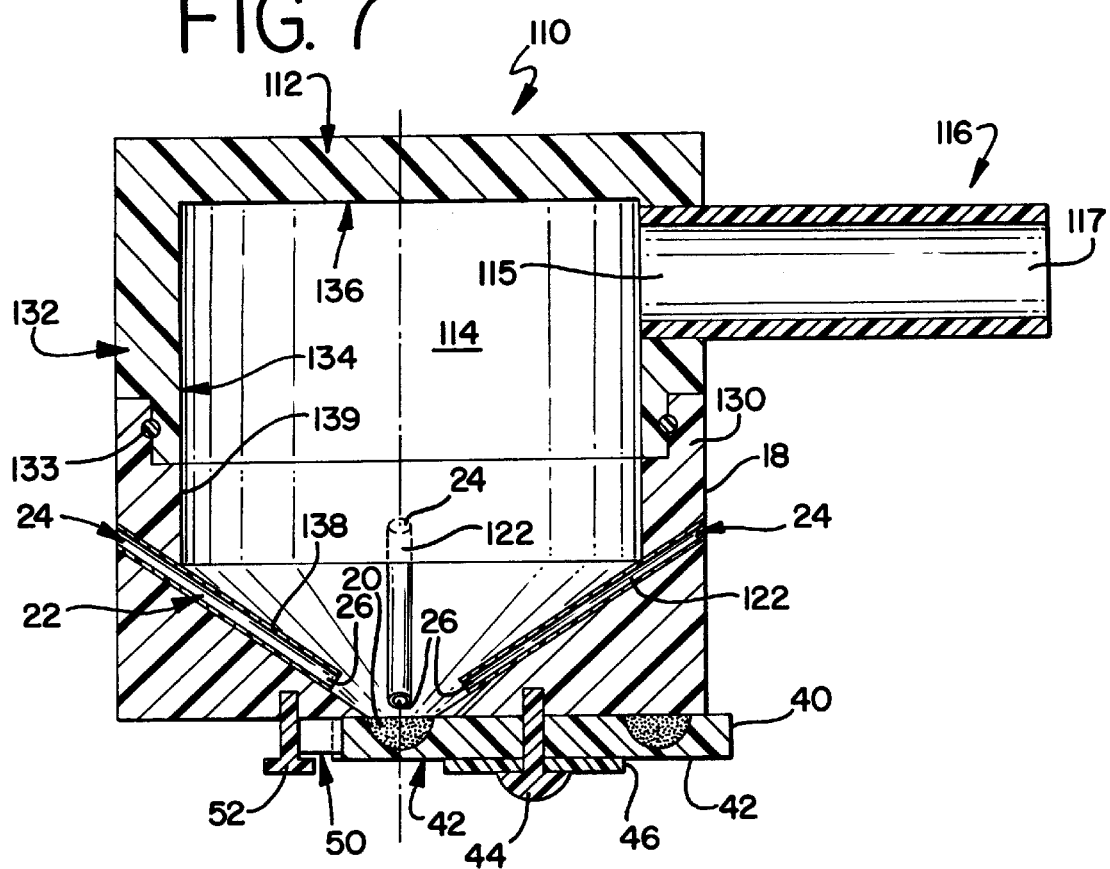
Figure 8:
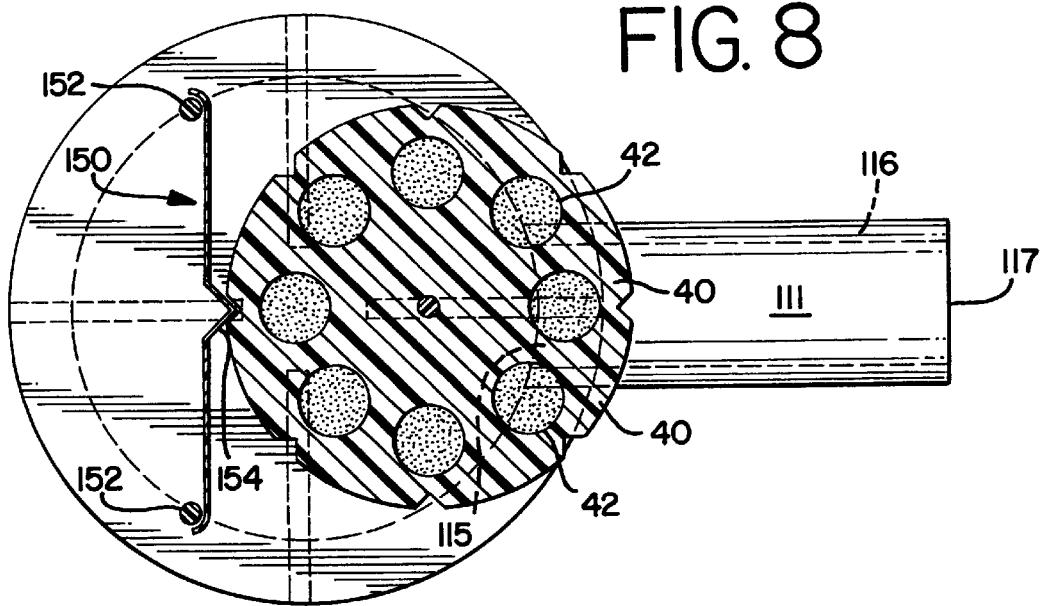
Figure 9:
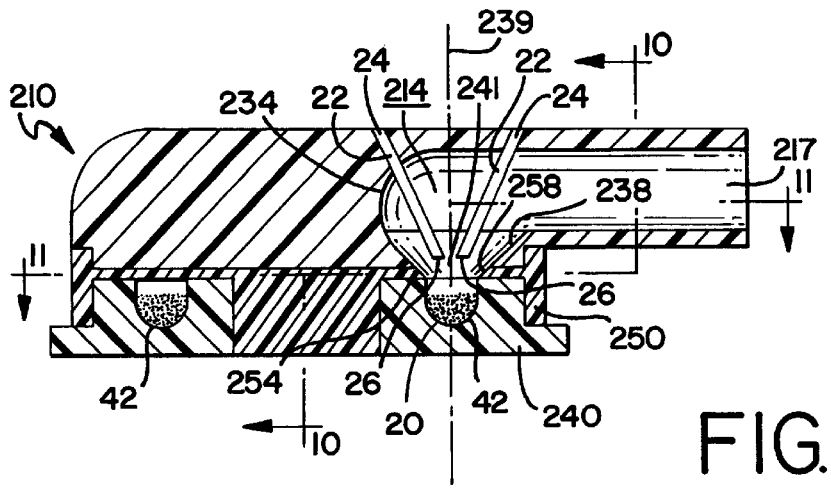
Figure 10:
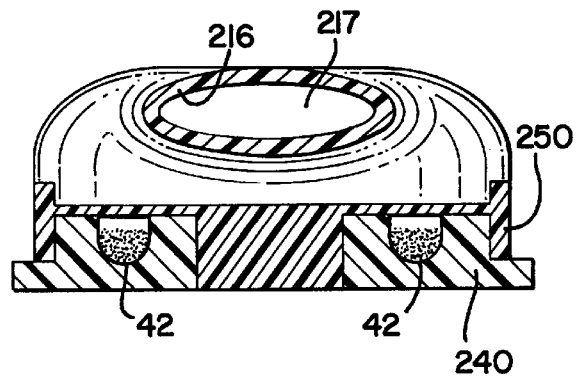
Figure 11:
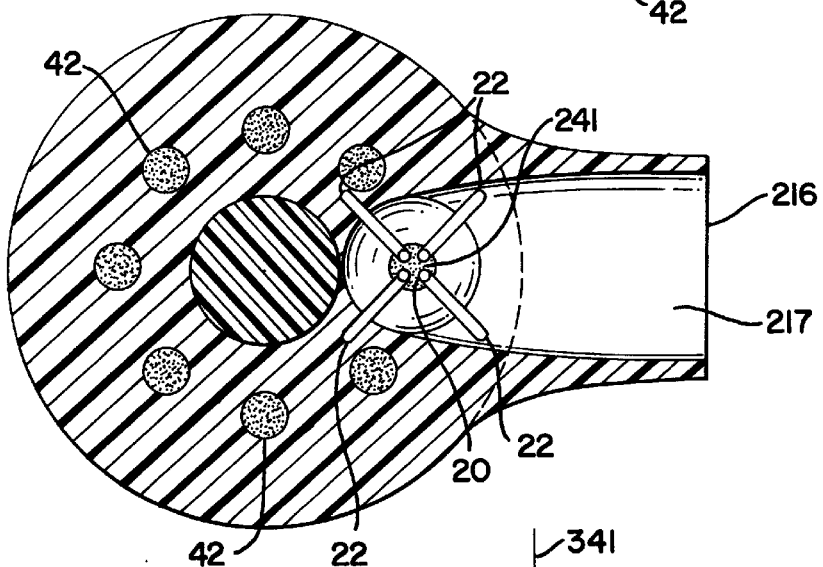

As shown in FIGS. 3 and 4, grooves 35 extend substantially radially upward from opening 41 formed at the bottom of the frusto-conical shaped lower portion. Opening 41 forms a cylindrical passageway that is in flow communication between the holding portion 20 and hold-up chamber 14. The air entry passageways 22, which are preferably configured as circular tube members, are supported by the grooves 35 in the lower portion such that the exit port 26 of the air entry passageways opens directly into the opening 41 at the edge thereof and is directed at the holding portion. In an exemplary embodiment, the exit port 26 is positioned a distance from the holding portion of from about 2.5 mm to about 3.0 mm. As shown in the embodiment of FIGS. 3–5 at least one of the exit ports 26 of the air entry passageways is slightly off-set from a longitudinally extending axis 39 of the opening 41 and the underlying holding portion 20, which is coaxial with the longitudinally extending axis of the hold-up chamber, whereby a cyclonic air flow is created within the chamber about the longitudinal axis 39. It should be understood by those of skill in the art that the cyclonic flow can be initiated without the aid of the angled walls. The tube members can be affixed in the groove formed in the lower portion using an adhesive or the like. Alternatively, the air entry passageways can be integrally formed in the lower portion as shown in the embodiment of FIG. 7, wherein the passageways 122 are provided immediately below the angled surface 138 of the lower portion 130.

As shown in FIG. 3, the upper portion 32 is provided with ceiling 36. Side walls 34 extend between angled walls 38 and ceiling 36. The upper portion has a cylindrical shape with a longitudinal axis 39 coaxial with the axis of opening 41.

Upon inhalation, air travels downwardly through passageways 22 and is directed at the substance in holding portion 20. By directing the air at the substance, the substance is removed from holding portion 20 and is therefore at least partially deaggregated if not substantially deaggregated upon the commencement of inhalation. Upon continued inhalation, the configuration and orientation of passageways 22 and/or the configuration of lower portion 30 of hold-up chamber 14 causes the air entering hold-up chamber 14 to adopt a cyclonic flow path.

Side walls 34 of hold-up chamber 14 may be of any particular configuration which does not inhibit the cyclonic or swirling flow of air in hold-up chamber 14. Accordingly, side walls 34 are preferably smooth and, in addition, are preferably of generally circular cross section. In one embodiment, side walls 34 are preferably of generally constant circular cross section so that hold-up chamber 14 may accordingly define a cylindrical chamber in inhaler 10. Similarly, ceiling 36 is preferably flat but can also be domed, indented or otherwise configured. Accordingly, once air commences to move in a cyclonic pattern in the lower portion of the hold-up chamber, this pattern will be maintained in the upper portion thereof. The continual movement of air in the upper portion of the hold-up chamber will keep the substance in motion so that the substance will generally not have an opportunity to aggregate. Further, the shear forces produced during the swirling action will assist in deaggregating those portions of the substance which were not deaggregated when the substance was removed from holding portion 20 upon the initial inhalation by the user.

Mouthpiece 16 is provided to draw off air from a portion of hold-up chamber 14 wherein the substance has been substantially deaggregated. The mouthpiece can be configured to be received in either the nose or the mouth of the user, or both. As shown in FIG. 3, the mouthpiece 16 includes an entry port 15 in flow communication with the hold-up chamber, an air exit passageway 11 and an exit port 17. The air passageway is preferably straight, although one of skill in the art should recognize that it could be curved, bent or otherwise configured. The mouthpiece also includes a rib 21 extending circumferentially about the outer surface of the mouthpiece. The external diameter of the mouthpiece tapers away from the rib. The tapered portion allows the mouthpiece to be press fit in an opening 9 provided in the upper portion 32 which communicates with the hold-up chamber 14 formed therein. The rib 21 limits the amount of insertion of the mouthpiece and also functions as an indicator to inform the user that their mouth is properly disposed about the mouthpiece. Mouthpiece 16 is preferably provided in upper portion 32 of hold-up chamber 14 and, more preferably, adjacent ceiling 36 of hold-up chamber 14. At this position, by the time the substance reaches the opening of mouthpiece 16, it has traveled several times around hold-up chamber 14 and is substantially, if not completely, deaggregated. For example, the combined initial deaggregation obtained by fluidizing the substance, and the subsequent further deaggregation produced by the cyclonic flow, can result in substance particle sizes of less than 5.8 microns being introduced into the mouthpiece.

It will further be appreciated that, due to the volume of hold-up chamber 14, not all of the substance will immediately exit hold-up chamber 14 upon initial inhalation by the user. Instead, as the inhalation continues, additional air will enter hold-up chamber 14 through passageways 22 and will dilute the substance remaining in hold-up chamber 14. This dilution of the concentration of the substance in hold-up chamber 14 is beneficial as it allows the substance to be slowly released during inhalation by the user. Therefore, the substance will be drawn in by the user during all portions of the inhalation and the substance will therefore travel to all regions of the lungs of the user. In addition, the deaggregation of the substance permits the substance particles to be drawn further into the lungs. However, if the volume of the hold-up chamber is too large, substance can be left in the device as the user's inhalation is exhausted prior to all of the fluidized substance being extracted. In an exemplary embodiment, the cylindrical portion of the hold-up chamber has an interior diameter of approximately 31.5 mm and the hold-up chamber has a volume of approximately 41,138 $mm^3$.

A further advantage of hold-up chamber 14 is that it allows for differing rates of air flow into and out of inhaler 10. In particular, the number and size of passageways 22 may be adjusted so as to provide a velocity of air flow into inhaler 10 sufficiently rapid to deaggregate or substantially deaggregate the substance in holding portion 20. Further, this flow rate of air is preferably sufficient to cause the deaggregation to occur substantially upon the commencement of inhalation by the user. This flow rate of air may also be sufficient to cause air entering the inhaler to undergo a cyclonic or swirling motion in the hold-up chamber or to at least assist in commencing such cyclonic or swirling motion.

In contrast, the air exit passageway of the mouthpiece 16 is sized with a cross-sectional flow area greater than the combined cross-sectional flow area of the air entry passageways so as to draw air from inhaler 10 at a rate sufficiently slow so that the substance fluidized in the air inhaled by a user will not substantially impact upon the throat and upper airway of the user. Thus, mouthpiece 16 will generally have a large cross-sectional area as compared to passageways 22. Preferably the ratio of the cross-sectional area of the air exit passageway relative to the cross-sectional area of the air entry passageway is greater than 10:1 and more preferably about 25:1. Therefore, the medicament will travel into the lungs of the user. In an exemplary embodiment, the inner diameter of the air exit passageway formed in the mouthpiece is about 17 mm, with a corresponding cross-sectional flow area of about 227 $mm^2$.

The present invention, with its fluidization and subsequent even and continuous administration of substance, ensures a minimal loss of substance during the administration of the substance. In particular, ratios of the emitted dose relative to the nominal dose between 0.7:1 and 1:1 can be obtained (with an ideal target ratio of 1:1), where the nominal dose is defined as the amount of substance initially carried by the holding portion and the emitted dose is defined as the amount of substance received by the user.

As is shown in FIG. 3, the cross-sectional flow area of the mouthpiece 16, or exit passageway, is preferably less than the cross-sectional area of the hold-up chamber, which can be defined as the cross-sectional area substantially perpendicular to the longitudinal axis 39 of the hold-up chamber. In the embodiment shown in FIG. 3, the cross-sectional area is measured across the cylindrical portion of the hold-up chamber. This configuration of the hold-up chamber and exit passageway of differing diameters helps to avoid the inhalation of a bolus, or highly concentrated or aggregated substance. In the absence of some restriction of the exit passageway as compared with the hold-up chamber, or some other alternative configuration between the exit passageway and the hold-up chamber, such as the non-parallel orientation of at least a portion of the exit passageway relative to the hold-up chamber and the swirling fluidized substance contained therein, the substance can potentially be inhaled immediately without substantial mixing such that the substance will not be drawn as far into the lungs. For example, the orientation of the exit passageway 11, which is preferably linear, is preferably substantially perpendicular to the longitudinal axis 39 about which the fluidized substance flows.

However, it is also desirable to provide as large a cross-sectional flow area as possible for the exit passageway 11 so as to reduce the velocity of the fluidized substance being received by the patient so as to thereby reduce the impaction on the back of the throat of the patient. But, it is also necessary that the patient be able to fit the mouthpiece 16 in their mouth. As shown in the embodiment of FIGS. 15 and 16, the mouthpiece has an elliptical configuration which maximizes the cross-sectional flow area, while still allowing the patient to insert the mouthpiece into their mouth.

Referring again to FIG. 20, a chart is shown with the velocity of air entering inhaler 10 measured against the number of tubes (with varying total cross sections as shown in FIG. 21). The total volume flow rate was maintained at 8 liters per minute and the resistance to flow was maintained at 0.3 cm of water per liter per minute. Resistance to flow is defined as the pressure drop across the inhalation device divided by the volume flow rate. As will be understood by one of skill in the art, the pressure drop is a function of the length and diameter of the air entry passageways. It is desirable, therefore, to provide as high an intake velocity as is possible, so as to ensure a fluidization of the medicament, while providing as low a resistance as possible so as to accommodate users capable of generating only relatively low volume flow rates. As can be seen when viewing FIG. 20, when inhaler 10 was provided with one tube having a total cross-sectional area of about 2.3 $mm^2$ (see FIG. 21), the flow rate was about 210 km per hour. When 8 tubes were provided, having a total cross-sectional area of about 6.4 $mm^2$ (see FIG. 21), the flow rate was reduced to about 75 km per hour. Accordingly, as the number of tubes, and the cross-sectional flow area increases, the flow rate of the air entering inhaler 10 through passageways 22 decreases. However, even with a large number of tubes, and the corresponding increase in cross-sectional flow area, the air flow rate may still be maintained at a velocity which would create substantial shear forces in inhaler 10 and which would cause the substance in holding portion 20 to be quickly fluidized.

FIG. 21 is a chart showing the total cross-sectional area of passageways 22 as the number of tubes decreases. As can be seen, the cross-sectional area of the tubes increases with the number of tubes which are provided. If the cross-sectional area increases too much with an increasing number of tubes, the diameter of some or all of the tubes may be decreased. By adjusting the diameter of passageways 22, and the number of passageways 22, the velocity of air entering inhaler 10 (for a given range of flow rates) may be maintained.

Figure 22:
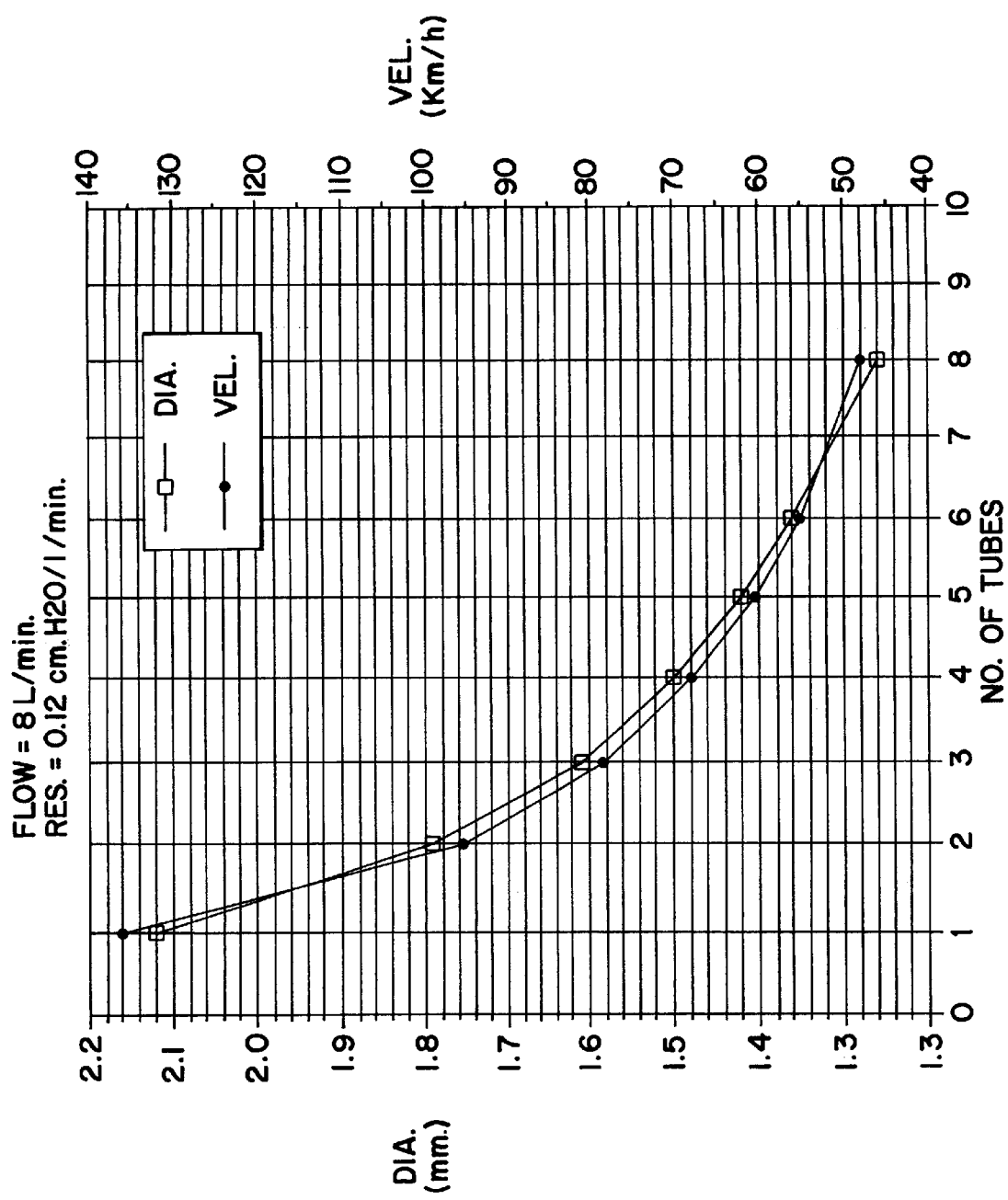
FIG. 22 is a graph of the diameter of tubes versus the number of tubes for an inhalation device having a total resistance to flow of 0.12 cm $H_2O$/l/min and at a constant flow rate of 8 l/min.

FIG. 22 is a chart showing the diameter of passageways 22 plotted against the number of tubes 22 in inhaler 10. As the number of tubes is increased, the diameter of the tubes is decreased. As the number of tubes (and their diameter) decrease, with a corresponding overall increase in cross-sectional flow area, the velocity of the air travelling through the tubes decreases from about 135 km per hour to about 48 km per hour. If the diameter of the tubes were decreased more, then a higher velocity may be maintained. Alternately, if a larger diameter in the tubes (and corresponding larger cross-sectional flow area) was provided, then the velocity would decrease.

Typically, users generate volume flow rates that can vary from relatively low flow rates (e.g., 8 liters per minute) to relative high flow rates (e.g., 120 liters per minute). As will be appreciated from these charts, even at a low flow rate (e.g., 8 liters per minute), a person with a breathing disability may still generate substantial velocities in passageways 22. These velocities are sufficient to deaggregate the substance 20. Conversely, due to the resistance of flow in passageways 22, a user without any breathing difficulties would be limited in the velocity which they could achieve in air travelling through passageways 22. For example, the present invention is capable of maintaining flow rates on the order of 10 liters per minute to 30 liters per minute, regardless of the lung capacity of the user. Accordingly, the inhaler 10 is adapted to be used by users who can generate low flow rates or high flow rates.

Similarly, a mouthpiece with a certain diameter may be employed for users having different lung capacities and flow rates. As mouthpiece 16 has a relatively large diameter as compared to passageways 22, the air exiting inhaler 10 will travel at a rate sufficiently slow so as to maintain, or at least substantially maintain, the substance in the air as the air travels through the mouth and upper airways of the user. Due to the large relative diameter of mouthpiece 16, a user would not generate a flow rate sufficiently fast so as to cause substantial quantities of substance to impact upon the throat and upper airways of the user.

As shown in FIGS. 2–5, inhaler 10 may be provided with a source of multiple doses of substance. For example, inhaler 10 may be provided with a container for holding bulk medicament and metering means for providing individual doses of medicament into holding portion 20 (not shown). Alternately, inhaler 10 may be provided with a plurality of individual doses of medicament. In yet another alternative, the inhaler can be configured to support a capsule containing a powdered substance. As shown in FIGS. 2–5, inhaler 10 includes a cassette 40 having provided therein a plurality of recesses 42, with each functioning as the holding portion 20 when it is moved to be in flow communication with the hold-up chamber. Each recess 42 is preferably sized to receive an individual dose of substance. Recesses 42 are preferably spaced in a circular pattern around cassette 40. Cassette 40 may be rotatably mounted to the bottom of inhaler 10 by means of bolt 44 and washer 46. Bolt 44 may pass through washer 46 and cassette 40 into lower portion 30 of inhaler 10. In this way, as cassette 40 is rotated, a different recess 42 is positioned below opening 41 of inhaler 10.

In order to maintain a particular recess 42 in alignment with opening 41, inhaler 10 may be further provided with a locking means. It should be understood that many types of mechanical devices are available for releasably locking the cassette relative to the housing, including, but not limited to, various detent mechanisms, set screws, ratchet mechanisms, etc. For example, the bottom of inhaler 10 may be provided with steel spring 50, which is secured to the bottom of inhaler 10 by means of bolts 52. As shown in FIGS. 4 and 5, the spring is a cantilever spring, although it should be understood that other types of springs, including, but not limited to, tension, compression and leaf springs would also work. Steel spring 50 is provided with a detent 54 which is adapted to engage a mating recess 53 which is provided on cassette 40. Accordingly, when a user needs to take a dose of substance, they may rotate cassette 40 to expose a new dose of substance. This dose of substance will be maintained in position by means of detent 54 of steel spring 50 and the mating recess on cassette 40. It will be appreciated by those skilled in the art that any substance holder or dispensing means may be adapted for use with inhaler 10. Further, if required, the substance may be sealed in individual doses and an opening means may be provided to open the individual substance container prior to inhalation by the user (not shown).

For the sake of simplicity, parts and features in various alternate embodiments that are substantially similar to parts and features previously referred to are identified with the same reference numbers.

FIGS. 6–8 show an alternative embodiment of the inhalation device similar to the device illustrated in FIGS. 1–5, but with some differences. For example, in this embodiment, the lower portion 130 includes a lower frusto-conical surface 138 mating with an upper cylindrical shaped interior surface 139. The lower portion is secured to the upper portion 132, which also preferably includes a cylindrical interior surface 134, so as to form a uniform cross-section for the hold-up chamber. The lower portion is secured to the upper portion in a snap-fit configuration with a detent mechanism 133, or similar securing mechanism. One of skill in the art should also understand that the upper and lower portions 132, 130 can be integrally formed. The frusto-conical portion opens directly into the holding portion 20. The mouthpiece shown in FIG. 7 opens into the hold-up chamber 114 immediately adjacent the ceiling 136 of the hold-up chamber and includes a relatively long air exit passageway 111 having entry and exit ports 115, 117. In addition, a spring 150 extends across the bottom of the housing and includes a detent 154 in the middle of the spring. The spring is secured at its ends with bolts 152 so as to function as a simply supported beam or leaf spring, rather than a cantilever spring as shown in the embodiment of FIGS. 1–5.

FIGS. 9–11 show an alternate embodiment of the inhaler. In this particular embodiment, inhaler 210 is again provided with four passageways 22. The four passageways are positioned at the four corners of a square so that there are opposed pairs of passageways 22.

In addition, hold-up chamber 214 is of a different construction. In this case, the lower portion of the hold-up chamber 214 is provided with an angled wall 238. However, sidewall 234 is concave. The lower portion of sidewall 234 which is opposed to angled wall 238 assists in creating a cyclonic flow of air about longitudinal axis 239 in hold-up chamber 214. In this embodiment, the hold-up chamber is configured so as to be positioned over the holding portion 20 nearest or proximate the mouthpiece. Also in this embodiment, the upper and lower portions of the hold-up chamber are formed substantially integrally in a single member. The holding portion 20 is formed in cassette 240 that is rotatably mounted to the housing with a carriage member 250. The carriage member 250 includes an opening 241 having an angled portion 258 mating with wall 238 and a concave portion 254 mating with wall 234. The mouthpiece 216 includes an elliptically shaped air exit passageway.

Figure 12:
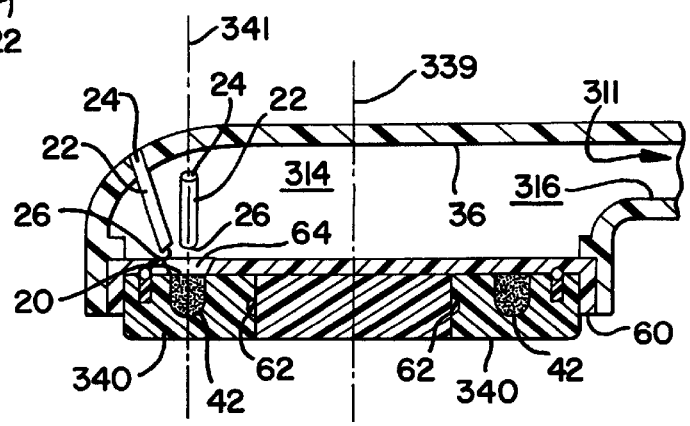

FIG. 12 shows an alternate inhaler. In this particular example, cover 60 is provided for cassette 340. In addition, detents 62 are provided to assist in maintaining recesses 42, or holding portions 20, in alignment with the opening 64. Cover 60 is a plate (which may be made of metal or plastic or the like) which is used to seal recesses 42. Cover 60 is provided with an opening 64, having a frusto-conical shape, which is positioned in alignment with portion 20. Accordingly, as cassette 340 is rotated, a different recess 42 may be positioned in alignment with opening 64 and holding portion 20 so that a new dose of substance is available for inhalation. Cover 60 may be required if the substance in recesses 42 is particularly sensitive to moisture (e.g. it will deteriorate upon exposure to moisture or its rate of aggregation may increase). Detents 62 may be protrusions provided on the lower surface of inhaler 10 to engage recesses provided in cassette 40. In the embodiment of FIG. 12, the holding portion 20 is exposed in a rear portion of the hold-up chamber distal from the air exit passageway 311 and has a longitudinal axis 341 extending parallel to but not coaxial with the longitudinal axis 339. Preferably, the hold-up chamber 314 has a circular cross-section so as to promote a cyclonic flow about longitudinal axis 339 therein.

Figure 13:
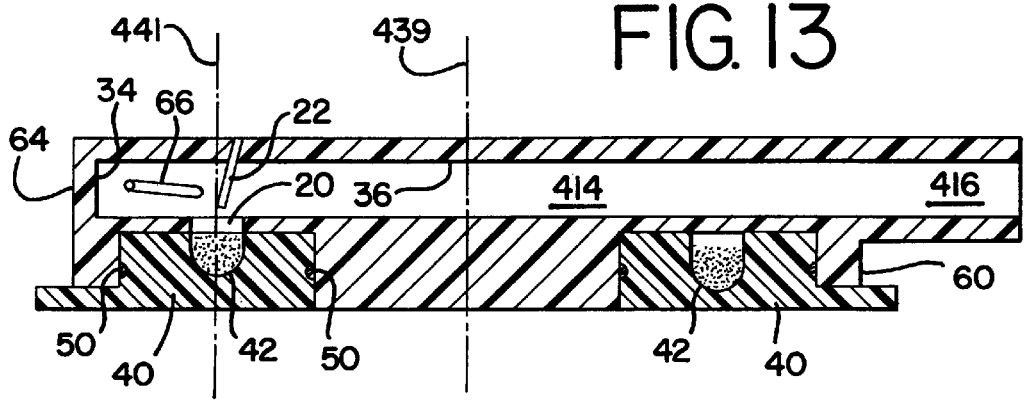

In the embodiment of FIG. 13, the inhaler is provided with a second set of one or more air entry passageways 66. Air entry passageways 66 are not aimed at the medicament in recess 42. Instead, passageways 66 are directed to provide a cross flow that assists in creating a cyclonic flow of air in hold-up chamber 414 about longitudinal axis 439 and further deaggregates the medicament as it swirls in the hold-up chamber. Accordingly, a portion of the air entering inhaler may be directed through air entry passageways 22 at the medicament and the remainder of the air entering inhaler 410 may pass through air entry passageways 66 so as to assist in creating, or to create, a cyclonic or swirling flow of air in hold-up chamber 414. The hold-up chamber 414 is preferably circular so as to promote the cyclonic flow therein. Therefore, although the mouthpiece 416 is shown as having a depth substantially the same as the hold-up chamber, the cross-sectional area of the air exit passageway is less than the cross-sectional area of the hold-up chamber, which extends longitudinally along axis 439. The air exit passageway also communicates with the hold-up chamber distal from the holding portion 20, or approximate the opposite end of the hold-up chamber. The holding portion 20 has a longitudinal axis 441 extending parallel to but not coaxial with longitudinal axis 439 of the hold-up chamber.

Figure 14:
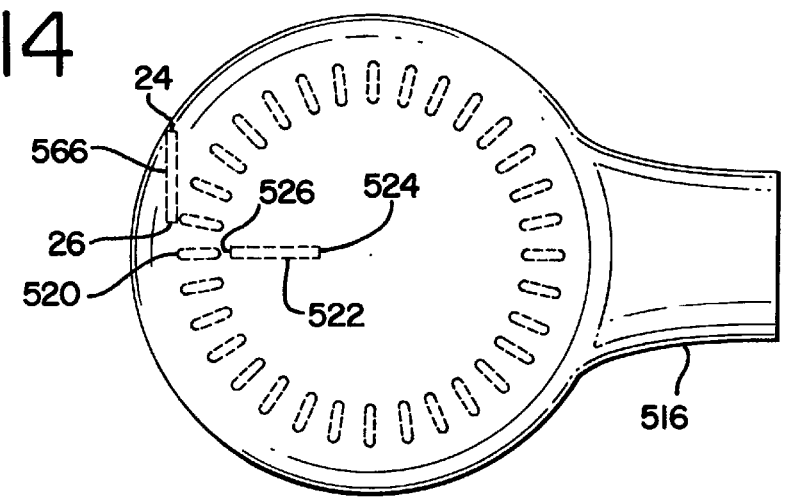
FIG. 14 is a top view of an alternative embodiment of the inhalation device.
Figure 15:
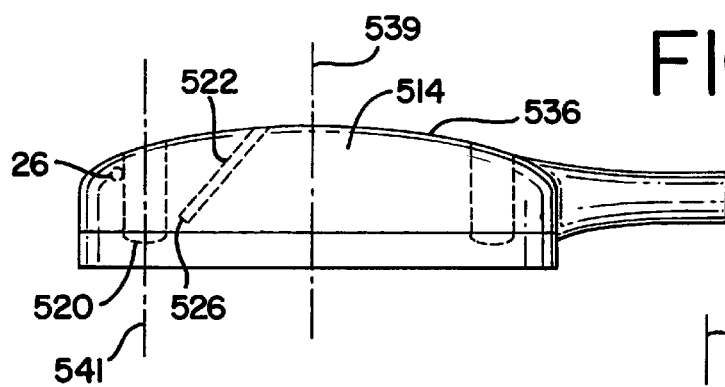
FIG. 15 is a side view of an alternative embodiment of the inhalation device shown in FIG. 14.
Figure 16:
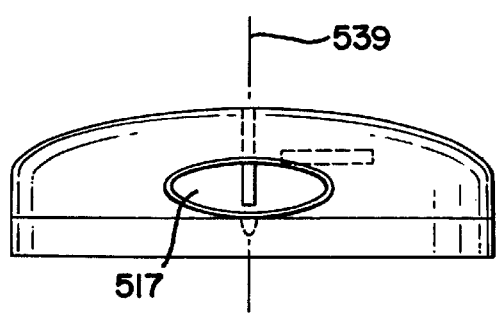
FIG. 16 is an end view of the inhalation device shown in FIG. 14.

Similarly, as shown in the embodiment of FIGS. 14–16, the hold-up chamber 514 has a generally circular cross-section and includes a generally cylindrically shaped lower portion and a domed or concave shaped ceiling 536. Two air entry passageways 522, 566 are provided. One passageway 522 has an exit port 526 positioned immediately adjacent and proximate to and directed at the holding portion so as to direct air to fluidize the medicament in the holding portion. A second passageway 566 is arranged substantially perpendicular to the longitudinal axis of the hold-up chamber 514 and tangential to the interior surface thereof such that air coming through the passageway promotes a cyclonic flow in the hold-up chamber about longitudinal axis 539, along which the hold-up chamber extends. In this embodiment, the holding portions 520, which are arranged circumferentially around the periphery of the carriage, are radially elongated with at least one of the holding portions aligned with the first air passageway 520 such that the air exiting the air passageway impinges upon the elongated holding portion to fluidize the substance and scoop the substance out of the holding portion directly into the path of the air exiting the second passageway 566 which further shears the substance so as to further deaggregate it and which also creates a cyclonic flow in the hold-up chamber. The holding portion 520 has a longitudinally extending axis 541 parallel to but not coaxial with the longitudinal axis 539 of the hold-up chamber. The mouthpiece 516 has an elliptically shaped exit port.

Figure 17:
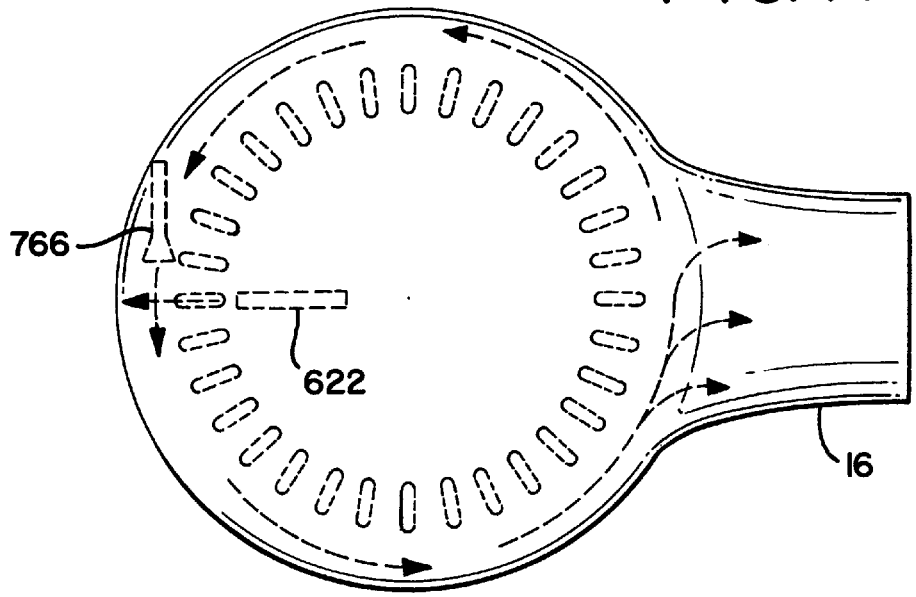
FIG. 17 is a top view of an alternate embodiment of the inhalation device.
Figure 18:
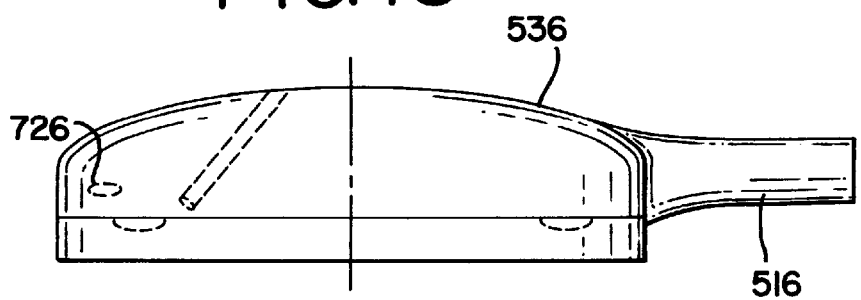
FIG. 18 is a side view of the inhalation device shown in FIG. 17.
Figure 19:
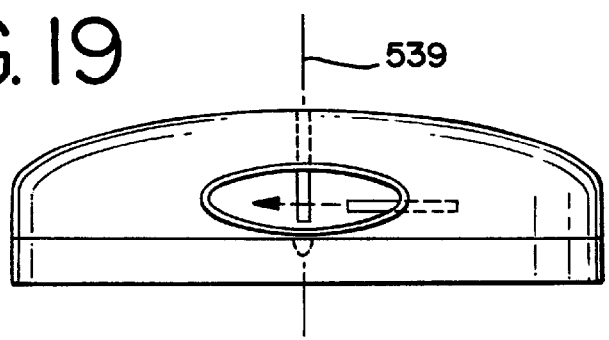
FIG. 19 is an end view of the inhalation device shown in FIG. 17.

In yet another embodiment, shown in FIGS. 17–19 the exit port 726 of the second air entry passageway 766 is flared, or has an elliptical cross-section that provides a greater area of directed air flow to further impact on the fluidized substance and to initiate the cyclonic flow in the hold-up chamber as illustrated by the flow directional arrows.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention. Therefore, it will be appreciated by those skilled in the art that various modifications and changes may be made to the instant inhaler without altering the nature of the invention.

What is claimed is:

1. An inhalation device for use in delivering a powdered substance to a user, the inhalation device comprising:

a hold-up chamber having a bottom;

a holding portion adapted to hold the substance, said holding portion opening into said bottom of said hold-up chamber in flow communication therewith;

an air entry passageway having an inlet port open to an exterior of said device, an exit port and a cross-sectional flow area, said exit port positioned above and directed downwardly at said holding portion, said exit port opening into said hold-up chamber proximate said holding portion opening into said bottom of said hold-up chamber; and an air exit passageway having a cross-sectional flow area greater than the cross-sectional flow area of said air entry passageway, said air exit passageway in flow communication with said hold-up chamber at a location spaced apart from said holding portion, said air exit passageway adapted to deliver the substance to the user;

whereby air enters said air entry passageway from said exterior of the device and is directed downwardly through said exit port of said air entry passageway at the holding portion so as to fluidize the substance upon inhalation by the user, and whereby said substance is maintained in a fluidized state in said hold-up chamber during inhalation and thereafter delivered to the user through said air exit passageway.

2. The inhalation device of claim 1 comprising a plurality of air entry passageways, said plurality of air entry passageways having a combined cross-sectional flow area less than the cross-sectional flow area of said air exit passageway.

3. The inhalation device of claim 1 wherein said hold-up chamber has a circular cross-section.

4. The inhalation device of claim 3 wherein said hold-up chamber has a longitudinally extending axis about which the substance is adapted to swirl in a fluidized state.

5. The inhalation device of claim 4 wherein said holding portion has a longitudinally extending axis parallel to and spaced apart from said longitudinal axis of said hold-up chamber.

6. The inhalation device of claim 4 wherein said hold-up chamber has a cylindrically shaped portion surrounding said longitudinal axis and a frusto-conically shaped portion extending from said cylindrical portion, said holding portion communicating with a bottom of said frusto-conically shaped portion.

7. The inhalation device of claim 4 wherein at least a portion of said air exit passageway is non-parallel to said longitudinal axis.

8. The inhalation device of claim 4 wherein said holding portion is positioned adjacent one end of said hold-up chamber and said exit passageway is longitudinally displaced from said holding portion adjacent the other end of said hold-up chamber.

9. The inhalation device of claim 2 wherein said holding portion has a longitudinally extending axis, and wherein the exit port of at least one of said air entry passageways is offset from said longitudinal axis of said holding portion.

10. The inhalation device of claim 1 wherein said ratio of said cross-sectional flow area of said exit passageways to said cross-sectional flow area of said entry passageway is greater than or equal to 10:1.

11. The inhalation device of claim 2 wherein at least one of said plurality of said air entry passageways directs air within the chamber to create a cyclonic flow therein.

12. The inhalation device of claim 1 further comprising a container having a plurality of holding portions, each of said holding portions adapted to hold a dose of substance, said container moveably connected to said chamber wherein said container can be moved to successively place at least one of said holding portions in communication with said hold-up chamber.

13. The inhalation device of claim 2 wherein said plurality of said air entry passageways comprises four air entry passageways.

14. The inhalation device of claim 1 wherein said holding portion is elongated and wherein said air entry passageway is positioned so as to direct air parallel to the length of said holding portion.

15. The inhalation device of claim 14 comprising a plurality of holding portions arranged circumferentially around a portion of said device, wherein said holding portions are radially elongated around said circumference of said portion of said device.

16. An inhalation device for use in delivering a powdered substance to a user, the inhalation device comprising:
   a hold-up chamber having a longitudinal axis about which the substance is adapted to swirl in a fluidized state;
   a holding portion adapted to hold the substance and opening into said hold-up chamber in flow communication therewith;
   at least one air entry passageway in flow communication with said hold-up chamber and open to an exterior of said device, said air entry passageway adapted to introduce air into said hold-up chamber; and
   an air exit passageway having at least a portion non-parallel to the longitudinal axis of said hold-up chamber, said air exit passageway in flow communication with said hold-up chamber and adapted to deliver the substance to the user.

17. The inhalation device of claim 16 wherein said air exit passageway is substantially perpendicular to said longitudinal axis of said hold-up chamber.

18. The inhalation device of claim 16 wherein said air exit passageway comprises an entry port and an exit port, said entry port opening into said hold-up chamber.

19. The inhalation device of claim 16 wherein said air entry passageway and said air exit passageway each have a cross-sectional flow area, said cross-sectional flow area of said air entry passageway being less than said cross-sectional flow area of said air exit passageway.

20. The inhalation device of claim 19 comprising a plurality of air entry passageways, said plurality of air entry passageways having a combined cross-sectional flow area less than the cross-sectional flow area of said air exit passageway.

21. The inhalation device of claim 16 wherein said hold-up chamber has a circular cross-section.

22. The inhalation device of claim 21 wherein said hold-up chamber has a cylindrically shaped portion centered about said longitudinally extending axis.

23. The inhalation device of claim 22 wherein said hold-up chamber has a frusto-conically shaped portion extending from said cylindrical portion, said holding portion communicating with a bottom of said frusto-conically shaped portion.

24. The inhalation device of claim 16 wherein said holding portion is positioned adjacent one end of said hold-up chamber and said air exit passageway is longitudinally displaced from said holding portion adjacent the other end of said hold-up chamber.

25. The inhalation device of claim 20 wherein at least one of said plurality of said air entry passageways directs air within the hold-up chamber to create a cyclonic flow therein.

26. The inhalation device of claim 16 further comprising a container having a plurality of holding portions, each of said holding portions adapted to receive a dose of medicament, said container moveably connected to said hold-up chamber wherein said container can be moved to successively place at least one of said holding portions in communication with said hold-up chamber.

27. An inhalation device for use in delivering a powdered substance to a user, the inhalation device comprising:
   a hold-up chamber having a cross-sectional area and a bottom;
   a holding portion adapted to hold the substance, said holding portion opening into said bottom of said hold-up chamber so as to be in flow communication therewith;
   an air entry passageway open to an exterior of said device and having an exit port and a flow cross-sectional area, said exit port positioned above and directed downwardly at said holding portion so as to direct air entering the inhalation device at the holding portion and to fluidize the substance upon inhalation by the user, said exit port opening into said hold-up chamber proximate said holding portion opening into said bottom of said hold-up chamber; and
   an air exit passageway having a flow cross-sectional area greater than the flow cross-section area of said air entry passageway and less than the cross-section area of said hold-up chamber, said exit passageway in flow communication with the hold-up chamber, said exit passageway adapted to deliver the substance to the user.

28. The inhalation device of claim 27 comprising a plurality of air entry passageways, said plurality of air entry passageways having a combined cross-sectional flow area less than the cross-sectional flow area of said air exit passageway.

29. The inhalation device of claim 27 wherein said hold-up chamber has a circular cross-section.

30. The inhalation device of claim 27 wherein said hold-up chamber has a longitudinally extending axis.

31. The inhalation device of claim 30 wherein said air exit passageway is non-parallel to said longitudinal axis of said hold-up chamber.

32. The inhalation device of claim 28 wherein at least one of said plurality of said air entry passageways directs air within the hold-up chamber to create a cyclonic flow therein.

33. The inhalation device of claim 27 further comprising a container having a plurality of holding portions, each of said holding portions adapted to receive a dose of substance, said container moveably connected to said hold-up chamber wherein said container can be moved to successively place at least one of said holding portions in communication with said hold-up chamber.

34. An inhalation device for use in delivering a powdered substance to a user, the inhalation device comprising:
   a hold-up chamber having a longitudinal axis about which the substance is adapted to swirl in a fluidized state and a bottom;
   a holding portion adapted to hold the substance, said holding portion opening into said bottom of said hold-up chamber so as to be in flow communication therewith;
   a first air entry passageway open to an exterior of said device and having an exit port and a cross-sectional flow area, said exit port positioned above and directed downwardly at said holding portion so as to direct air entering the inhalation device at the holding portion and to fluidize the substance upon inhalation by the user;
   a second air entry passageway having an exit port and a cross-sectional flow area, said exit port of said second air entry passageway positioned above said holding portion and directed substantially perpendicular to the longitudinal axis of the hold-up chamber at a location spaced from the holding portion; and
   an air exit passageway having a flow cross-sectional area greater than the combined cross-section flow areas of said first and second air entry passageways, said air exit passageway in flow communication with the hold-up chamber and adapted to deliver the substance to the user.

35. A method for delivering a powdered substance to a user, said method comprising:
   providing an inhalation device having an exterior and comprising a holding portion with a nominal dosage of said substance disposed thereon, a hold-up chamber in flow communication with said holding portion, said holding portion opening into a bottom of said hold-up chamber, an air entry passageway in flow communication with said hold-up chamber, said air entry passageway comprising an inlet port open to said exterior of said device and an exit port positioned above and directed downwardly at said holding portion, said exit port opening into said hold-up chamber proximate said holding portion opening into said bottom of said hold-up chamber, and an air exit passageway in flow communication with said hold-up chamber at a location spaced from said holding portion;
   fluidizing said substance by inhaling through said air exit passageway and thereby directing air through said air entry passageway at a first velocity at said holding portion, wherein said air directed through said air entry passageway is generated solely by said inhaling through said air exit passageway;
   maintaining said substance in a fluidized state in said hold-up chamber by swirling said fluidized substance within said hold-up chamber;
   delivering an emitted dose of said fluidized substance to said user at a second velocity through said air exit passageway in flow communication with said hold-up chamber, wherein said second velocity is less than said first velocity.

36. The method of claim 35 wherein said first velocity is greater than or equal to about 40 km/hr.

37. The method of claim 35 wherein said second velocity is less than or equal to about 10 km/hr.

38. The method of claim 35 wherein said ratio of said nominal dose to said emitted dose is between about 2:1 and about 1:1.

39. The method of claim 35 wherein said inhalation device comprises a plurality of said air entry passageways, said plurality of air entry passageways having a combined cross-sectional flow area less than a cross-sectional flow area of said air exit passageway.

40. The method of claim 35 wherein said hold-up chamber has a longitudinal axis, and wherein said maintaining said medication in a fluidized state comprises swirling said substance about said longitudinal axis.

41. The method of claim 40 wherein at least a portion of said hold-up chamber has a circular cross-section and wherein at least one of said air entry passageways is directed tangentially to said circular cross-section so as to create a cyclonic flow in said hold-up chamber about said longitudinal axis.

42. The method of claim 35 wherein said hold-up chamber has a cylindrically shaped portion and a frusto-conically shaped portion extending from said cylindrical portion, said holding portion in flow communication with a bottom of said frusto-conically shaped portion.

43. The method of claim 40 wherein said air exit passageway is non-parallel to said longitudinal axis.

44. The method of claim 35 wherein said holding portion is positioned adjacent one end of said hold-up chamber and said air exit passageway is longitudinally displaced from said holding portion adjacent the other end of said chamber.

* * * * *

UNITED STATES PATENT AND TRADEMARK OFFICE
CERTIFICATE OF CORRECTION

PATENT NO.    : 6,116,239
DATED         : September 12, 2000
INVENTOR(S)   : George Volgyesi It is certified that error appears in the above-identified patent and that said Letters Patent is hereby corrected as shown below:

U.S. PATENTS

| U.S. Patent No. | Issue Date | Patentee |
| --- | --- | --- |
| 1,756,254 | 4/1930 | Lykken |
| 2,515,542 | 7/1950 | Yellott |
| 2,517,482 | 7/1950 | Hall |
| 3,271,162 | 9/1966 | Bishop |
| 3,362,405 | 1/1968 | Hazel |
| 3,565,348 | 2/1971 | Dickerson, et al. |
| 3,568,887 | 3/1971 | Jacobs, et al. |
| 3,625,403 | 12/1971 | Rousselot |
| 3,726,484 | 4/1973 | Schurr |
| 3,795,244 | 3/1974 | Lax et al. |
| 3,809,084 | 5/1974 | Hansen |
| 3,870,046 | 3/1975 | Elliott |
| 3,915,165 | 10/1975 | Rambosek et al. |
| 3,918,451 | 11/1975 | Steil |
| 3,991,761 | 11/1976 | Cocozza |
| 4,206,758 | 6/1980 | Hallworth et al. |
| 4,249,526 | 2/1981 | Dean et al. |
| 4,423,724 | 1/1984 | Young |
| 4,429,835 | 2/1984 | Brugger et al. |
| 4,452,239 | 6/1984 | Malem |
| 4,706,663 | 11/1987 | Makiej |
| 4,762,148 | 8/1988 | Marui et al. |
| 4,884,565 | 12/1989 | Cocozza |
| 4,907,583 | 3/1990 | Wetterlin et al. |
| 4,940,051 | 7/1990 | Lankinen |
| 5,035,364 | 7/1991 | Escallon |
| 5,165,391 | 11/1992 | Chiesi et al. |
| 5,186,166 | 2/1993 | Riggs et al. |

FOREIGN REFERENCES

| Document No. | Publication Date | Country |
| --- | --- | --- |
| EP 0 005 585 | 11/1979 | EPO |
| EP 0 215 559 | 3/1987 | EPO |
| FR 552,542 | 5/1923 | France |
| FR 777,286 | 2/1935 | France |
| FR 1,445,520 | 10/1966 | France |

UNITED STATES PATENT AND TRADEMARK OFFICE
CERTIFICATE OF CORRECTION

PATENT NO. : 6,116,239
DATED : September 12, 2000
INVENTOR(S) : George Volgyesi

It is certified that error appears in the above-identified patent and that said Letters Patent is hereby corrected as shown below:

| | | |
|---|---|---|
| DT 2449179 | 11/1976 | Germany |
| DE 3216022 | 11/1982 | Germany |
| DE 3612473 | 10/1987 | Germany |
| 556532 | 2/1957 | Italy |
| SU 0990303 | 2/1983 | USSR |
| SU 1282894 | 1/1987 | USSR |
| SU 1503827 | 6/1989 | USSR |
| 12,823 | 2/1913 | Great Britain |
| GB 240,358 | 10/1925 | Great Britain |
| GB 1,331,216 | 9/1973 | Great Britain |
| GB 1,396,258 | 6/1975 | Great Britain |
| GB 2,064,334 | 6/1981 | Great Britain |
| WO 83/01915 | 6/1983 | WIPO |
| WO 88/02267 | 4/1988 | WIPO |
| WO 88/03419 | 5/1988 | WIPO |
| WO 91/19524 | 12/1991 | WIPO |

Signed and Sealed this

Twenty-fifth Day of September, 2001

Attest:

NICHOLAS P. GODICI
*Attesting Officer*   Acting Director of the United States Patent and Trademark Office